US012767929B2

(12) United States Patent
Weinacht et al.

(10) Patent No.: US 12,767,929 B2
(45) Date of Patent: Oct. 20, 2026

(54) GENERATION OF INDUCED HUMAN THYMIC EPITHELIAL CELLS AND ITS APPLICATION IN CELL-BASED IMMUNOTHERAPIES

(71) Applicant: The Board of Trustees of the Leland Stanford Junior University, Stanford, CA (US)

(72) Inventors: Katja G. Weinacht, Stanford, CA (US); Hui Gai, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 556 days.

(21) Appl. No.: 18/261,471

(22) PCT Filed: Jan. 13, 2022

(86) PCT No.: PCT/US2022/012255
§ 371 (c)(1),
(2) Date: Jul. 13, 2023

(87) PCT Pub. No.: WO2022/155291
PCT Pub. Date: Jul. 21, 2022

(65) Prior Publication Data

US 2024/0076618 A1 Mar. 7, 2024

Related U.S. Application Data

(60) Provisional application No. 63/138,208, filed on Jan. 15, 2021.

(51) Int. Cl.
*C12N 5/078* (2010.01)

(52) U.S. Cl.
CPC ........ *C12N 5/065* (2013.01); *C12N 2501/999* (2013.01); *C12N 2506/45* (2013.01)

(58) Field of Classification Search
IPC ........................ C12N 5/065,2501/999, 2506/45
See application file for complete search history.

(56) References Cited

U.S. PATENT DOCUMENTS

| | | | |
|---|---|---|---|
| 9,234,170 | B2 | 1/2016 | Snoeck et al. |
| 9,719,067 | B2 | 8/2017 | Snoeck et al. |
| 9,850,465 | B2 | 12/2017 | Parent et al. |
| 10,487,313 | B2 | 11/2019 | Funa et al. |
| 2003/0138951 | A1 | 7/2003 | Yin |
| 2016/0010055 | A1 | 1/2016 | Parent et al. |
| 2016/0237401 | A1 | 8/2016 | Vallier et al. |

FOREIGN PATENT DOCUMENTS

| | | | | |
|---|---|---|---|---|
| CA | 2902857 | A1 | 9/2014 | |
| WO | WO-2014134213 | A1 * | 9/2014 | ............ C12N 5/065 |
| WO | WO-2020205859 | A1 * | 10/2020 | ............. A61P 37/00 |
| WO | WO2020220040 | A1 | 10/2020 | |

OTHER PUBLICATIONS

Kearns, Nicola A. “Generation of Pharyngeal Foregut Endoderm from Pluripotent Stem Cells.” (2017). (Year: 2017).*
B27 Serum Free Supplement. ThermoFisher. (Year: 2025).*
Application No. PCT/US2022/012255, International Preliminary Report on Patentability, Mailed On Jul. 27, 2023, 9 pages.
Application No. PCT/US2022/012255, International Search Report and Written Opinion, Mailed On Jun. 9, 2022, 13 pages.
Hassan et al. (2017) “A simple method to isolate and expand human umbilical cord derived mesenchymal stem cells: using explant method and umbilical cord blood serum.” International Journal of Stem Cells, vol. 10, No. 2, pp. 184-192.
Inami et al., (2011) “Differentiation of induced pluripotent stem cells to thymic epithelial cells by phenotype.” Immunology and Cell Biology, vol. 89, No. 2, pp. 314-321.
Mccracken et al., (2014) “Mechanisms of endoderm patterning and directed Differentiation of human stem cells into foregut tissues.” PHD Thesis, University of Cincinnati, Medicine: Molecular and Developmental Biology, pp. 1-184.
Nakajima et al., (2019) “In vitro generation of somite derivatives from human induced pluripotent stem cells.” Journal of Visualized Experiments, No. 146, pp. 1-12.
Otsuka et al., (2020) “Efficient generation of thymic epithelium from induced pluripotent stem cells that prolongs allograft survival.” Scientific Reports, vol. 10, No. 1.
Parent et al., (2023) “Generation of functional thymic epithelium from human embryonic stem cells that supports host T cell development.” Cell Stem Cell, vol. 13, No. 2, pp. 219-229.
Rankin et al., (2018) “Timing is everything: Reiterative Wnt, BMP and RA signaling regulate developmental competence during endoderm organogenesis.” Developmental Biology, vol. 434, No. 1, pp. 121-132.
Slepicka et al., (2022) “Functional Human iPSC-Derived Thymic Epithelial Progenitor Cells Reconstitute T Cell Development and Function in an In Vivo Model of Thymic Aplasia.” Blood, vol. 140, Supplement No. 1, pp. 7340-7341.
Yoon et al., (2012) “Sunitinib synergizes the antitumor effect of cisplatin via modulation of ERCC1 expression in models of gastric cancer.” Cancer Letters, vol. 321, No. 2, pp. 128-136.
Park et al. (2021) “A cell atlas of human thymic development defines T cell repertoire formation” Science, 367(6480): doi:10.1126/science.aay3224.
Yayon et al. (2024) “A spatial human thymus cell atlas mapped to a continuous tissue axis” Nature, 635:708-718.

* cited by examiner

*Primary Examiner* — Peter Paras, Jr.
*Assistant Examiner* — Fatimah Khalaf Matalkah
(74) *Attorney, Agent, or Firm* — Brian E. Davy; Bozicevic, Field & Francis LLP

(57) ABSTRACT

Methods of differentiating pluripotent stem cells into thymic epithelial progenitor cells are provided.

18 Claims, 6 Drawing Sheets

Overview of the differentiation protocol

Induction of DE and AFG cells using published protocols

Expression of characteristic markers during stepwise differentiation

FIG. 4A-B

Expression of markers specific to bipotent PPEIII: HOXA3 and TBX1
- Dynamic temporal change under treatment with various combinatorial signals FIG.6A-B
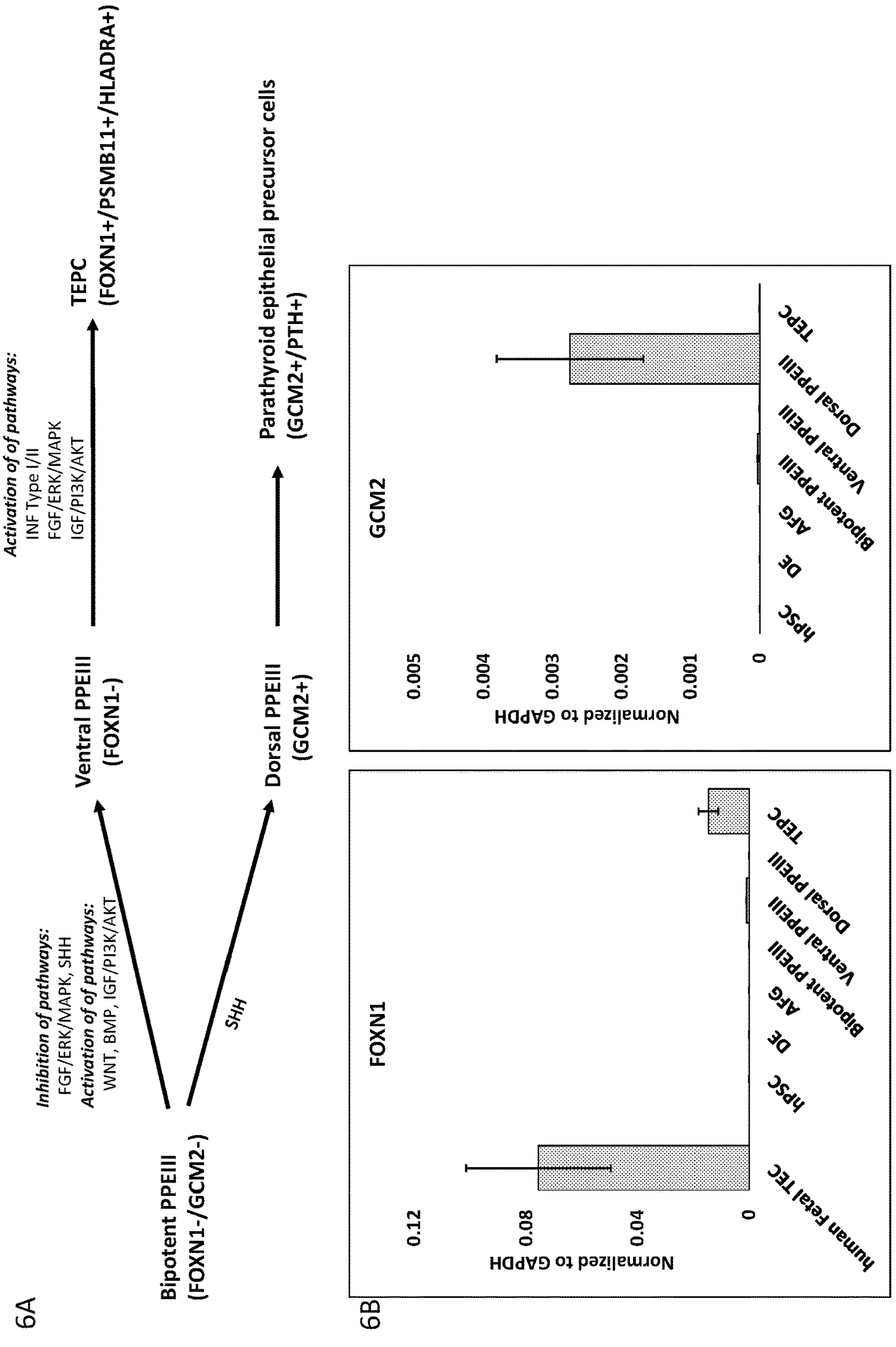

GENERATION OF INDUCED HUMAN THYMIC EPITHELIAL CELLS AND ITS APPLICATION IN CELL-BASED IMMUNOTHERAPIES

CROSS-REFERENCE TO RELATED PATENT APPLICATIONS

The present patent application is a U.S. National Phase 371 of PCT/US2022/012255, filed on Jan. 13, 2022, which claims benefit of priority to U.S. Provisional Patent Application No. 63/138,208, filed Jan. 15, 2021, each of which is incorporated by reference for all purposes.

BACKGROUND OF THE INVENTION

Thymus organogenesis is among the most complex processes in human development. Human embryogenesis starts with egg fertilization, followed by blastocyst formation and implantation into the uterus. Cells in the blastocyst are organized in a cluster called inner cell mass (ICM), which gives rise to three germ layers: endoderm, mesoderm and ectoderm.

Thymus is derived from endoderm, beginning with the formation of an embryonic gut tube composed of multipotent endodermal progenitor cells organized along the cranial-caudal and ventral-dorsal axis. Thymus, parathyroid, lung and esophagus arise in close proximity in the cranial portion of the gut tube.

Environmental cues including soluble gradient signaling and direct cell-cell interactions induce these progenitor cells to commit to different endodermal organ lineages. As development proceeds, four pharyngeal pouches are formed at the cranial end of the gut tube, separated by surrounding mesoderm and ectoderm tissues. Within the pharyngeal region, endodermal progenitor cells interact with cranial neural crest cells and mesodermal cells through sequential and dynamic signaling to induce thymic organogenesis. During week 6 of embryonic development thymic anlage arises in the ventral third pharyngeal pouch. These thymic epithelial progenitor cells (TEPCs) are characterized by strong FOXN1 gene expression and are cytokeratin 5 (KRT5) and cytokeratin 8 (KRT8) double positive (Farley, Morris et al. 2013). These TEPCs can further differentiate into functionally distinct cortical thymic epithelial cells (eTECs) and medullary thymic epithelial cells (mTECs) to instruct T cell development through positive selection, negative selection and central tolerance induction.

The thymus is a primary lymphoid organ that plays a critical role in the development of adaptive T cell immunity and central tolerance. Bone marrow-derived common lymphoid progenitor cells (CLPs) migrate into the thymus where they interact with TECs. Once migrated into the thymus, CLPs are referred to as thymocytes. Thymus-resident TECs stimulate thymocytes to proliferate and mature. In addition, TECs define the T-cell receptor (TCR) repertoire of thymocytes through sequential positive and negative selection of thymocytes based on affinity of the TCR to self-peptides presented on major histocompatibility complex (MHC) class I and II of TECs. Mature T cells that have undergone the thymic selection process express a diverse. MHC-restricted and self-tolerant TCR repertoire that protects against infection and prevents autoimmunity. Accordingly, compromise of thymic function can manifest in immunodeficiency, autoimmunity, malignancy, and death (Abramson and Anderson 2017).

Thymic function can be impaired in various congenital or acquired conditions. Patients born with congenital thymic aplasia, due to 22q11 Deletion Syndrome, or mutations in TBX1, FOXN1 or CHD7, can present with complete absence of T cells and a severe combined immunodeficiency (SCID)-like phenotype (Du, de la Morena et al. 2019, Du, Huynh et al. 2019, Giardino, Borzacchiello et al. 2020, Yamazaki, Urrutia et al. 2020). During hematopoietic stem cell transplantation (HSCT), acute graft-versus-host disease (aGVHD) can cause severe thymic injury in the recipient leading to impaired T cell reconstitution and increased risk of morbidity and mortality after HSCT (Seddik. Seemayer et al. 1980). Thymic function can also be compromised by infection, tumor, irradiation, or iatrogenic surgical removal due to cardiac surgeries (Chung, Barbara-Bumham et al. 2001, Krenger, Blazar et al. 2011). The thymus' role in building immune identity and function begins long before birth. The thymus peaks in size in infancy and then structurally disappears over time (Abramson and Anderson 2017). Aging reduces thymic function drastically and results in immune senescence in the elderly. The absence of effective T cell responses in the elderly (immune senescence) explains their susceptibility to infections with novel antigens such as SARS-CoV-2 (Weiskopf, Weinberger et al. 2009, Elyahu and Monsonego 2021). Due to inadequate viral eradication by T cells, morbidity and mortality associated with COVID-19 is much higher in the elderly (Kellogg and Equils 2020).

The thymus has no known endogenous capacity to regenerate. Therefore, the concept of thymic transplantation serves as an ultimate solution to treat thymic defects under different causes. In the case of 22q11 Deletion Syndrome, allogenic postnatal thymus transplantation has provided proof of principle that HLA-unmatched pediatric donor thymic tissues can lead to successful immune reconstitution with the emergence of a diverse TCR V-beta repertoire (Markert, Boeck et al. 1999, Markert, Devlin et al. 2007). However, post-transplant organ-specific autoimmunity remains a major concern (Davies, Cheung et al. 2017). Currently allogeneic thymus transplantation is only available to a very small number of patients at one center in the US and one center in the UK, leaving an unmet clinical need for patients born without thymus. Lack of histocompatibility-matching limits allogenic thymic transplantation to patients with complete absence of the thymus. In patients with residual thymic function, preformed T-cells would reject the transplanted tissue unless the patients were medically immunosuppressed. Patient-specific or histocompatible thymic tissues derived from pluripotent stem cells could address the critically unmet need. Importantly, beyond its use for thymic reconstitution in 22q11 Deletion Syndrome and other genetic syndromes presenting with thymic aplasia/hypoplasia, transplantation of functional thymic tissue has a much broader range of clinical applications in conditions in which thymic function is compromised or requires modulation, specifically but not limited to, its use after HSCT to promote T cell immune reconstitution, for induction of tolerance in the setting of donor organ transplantation, and to augment the declining immune function during aging (immune senescence).

BRIEF SUMMARY OF THE INVENTION

In some embodiments, methods of differentiating a Definitive Endoderm (DE) cell or an Anterior Foregut (AFG) cell or an Anterior Foregut (AFG)-plus cell, as defined below, to a HOXA3+, TBX1+/high, bipotent PPEIII cell that has a committed fate to PPEIII and has the potency to further differentiate into thymus and parathyroid epithelial lineages, are provided. In some embodiments, the method comprises culturing the DE cell or AFG cell or AFG-plus cell in a medium comprising at least: a Transforming Growth Factor (TGF-β) signaling pathway inhibitor; a Bone Morphogenic Protein (BMP) signaling pathway inhibitor; a Retinoic Acid (RA) signaling pathway activator; a PI3K/AKT signaling pathway inhibitor, wherein the culturing of the DE or AFG or AFG-plus cell promotes differentiation to a bipotent PPEIII cell specified for PPEIII and primed for thymus or parathyroid fate.

In some embodiments, the medium further comprises a Fibroblast Growth Factor (FGF) signaling pathway activator. In some embodiments, the medium further comprises a canonical WNT signaling pathway inhibitor.

In some embodiments, the method further comprises differentiating the HOXA3+, TBX1+/high bipotent PPEIII cell into a human TBX1 dim, PAX1+, PAX9+, FOXG1+ ventral PPEIII cell by culturing the bipotent PPEIII cell in a second medium comprising: a WNT signaling pathway activator; a BMP signaling pathway activator; wherein the culturing promotes differentiation of the bipotent PPEIII cell to a ventral PPEIII cell.

In some embodiments, the second medium further comprises one, some or all of the following: an FGF/ERK/MAPK signaling pathway inhibitor, an IGF signaling pathway activator, and a Sonic Hedgehog (SHH) signaling pathway inhibitor. In some embodiments, the second medium comprises an FGF/ERK/MAPK signaling pathway inhibitor. In some embodiments, the second medium comprises an IGF signaling pathway activator. In some embodiments, the second medium comprises a Sonic Hedgehog (SHH) signaling pathway inhibitor.

In some embodiments, the method further comprises differentiating the ventral PPEIII cell to a FOXN1+, PSMB11+, EPCAM+ TEPC cell, wherein the differentiation protocol comprises culturing the ventral PPEIII cell in a third medium comprising: an IFN type I or II signaling pathway activator, a FGF signaling pathway activator; and an IGF signaling pathway activator.

In some embodiments, the third medium further comprises one, some or all three of the following: a Sonic Hedgehog (SHH) signaling pathway inhibitor, a canonical WNT signaling pathway inhibitor and a RANK ligand.

In some embodiments, the DE or AFG cell is a primary DE or AFG cell, respectively.

In some embodiments, the method comprises obtaining the DE cell or AFG cell from a human.

In some embodiments, the method comprises introducing the bipotent PPEIII cell, ventral PPEIII cell, or TEPC cell into a human.

In some embodiments, the bipotent PPEIII cell, ventral PPEIII cell, or TEPC cell is autologous to the human individual. In some embodiments, the bipotent PPEIII cell, ventral PPEIII cell, or TEPC cell is allogenic to the human individual.

In some embodiments, the human has congenital thymic aplasia, thymic injury, reduced thymic function (e.g., due to HSCT status, aGVHD, infection, tumor, irradiation, medications or iatrogenic surgical removal due to cardiac surgeries), or age-related decline in thymic function.

Also provided are methods of differentiating a HOXA3+, TBX1+/high, bipotent PPEIII cell to a TBX1 dim, PAX1+, PAX9+ FOXG1+ ventral PPEIII cell that can further differentiate into thymic epithelial progenitor cells. In some embodiments, the method comprises culturing the bipotent PPEIII cell in a medium comprising at least: a WNT signaling pathway activator; a BMP signaling pathway activator, wherein the culturing promotes differentiation of the bipotent PPEIII cell to a ventral PPEIII cell.

In some embodiments, the medium further comprises one, some or all of the following: an FGF/ERK/MAPK signaling pathway inhibitor, an IGF signaling pathway activator, and a Sonic Hedgehog (SHH) signaling pathway inhibitor. In some embodiments, the medium comprises an FGF/ERK/MAPK signaling pathway inhibitor. In some embodiments, the medium comprises an IGF signaling pathway activator. In some embodiments, the medium comprises a Sonic Hedgehog (SHH) signaling pathway inhibitor.

In some embodiments, the method comprises introducing the bipotent PPEIII cell, ventral PPEIII cell, or TEPC cell into a human.

In some embodiments, the bipotent PPEIII cell, ventral PPEIII cell, or TEPC cell is autologous to the human individual. In some embodiments, the bipotent PPEIII cell, ventral PPEIII cell, or TEPC cell is allogenic to the human individual.

Also provided are methods of differentiating a TBX1dim, PAX1+, PAX9+ FOXG1+ ventral PPEIII cell to a FOXN1+, PSMB11+, EPCAM+ TEPC cell. In some embodiments, the method comprises culturing the ventral PPEIII cell in a medium comprising at least: an IFN type I or II signaling pathway activator: a FGF signaling pathway activator: and an IGF signaling pathway activator. In some embodiments, the medium further comprises one, both or all three of the following: a Sonic Hedgehog (SHH) signaling pathway inhibitor and/or a canonical WNT signaling pathway inhibitor and/or a RANKL.

Also provided is a human cell culture medium comprising ingredients including: a Transforming Growth Factor (TGF-62 ) signaling pathway inhibitor; a Bone Morphogenic Protein (BMP) signaling pathway inhibitor; a Retinoic Acid (RA) signaling pathway activator; a PI3K/AKT signaling pathway inhibitor; wherein the ingredients are in sufficient concentration to promote differentiation of a Definitive Endoderm (DE) cell or Anterior Foregut (AFG) cell or Anterior Foregut-plus (AFG-plus) cell to a HOXA3+, TBX1+/high, bipotent PPEIII cell.

In some embodiments, the medium further comprises human primary or pluripotent stem cell (PSC)-derived AFG or DE cells. In some embodiments, the medium further comprises a Fibroblast Growth Factor (FGF) signaling pathway activator. In some embodiments, the medium further comprises a canonical WNT signaling pathway inhibitor.

Also provided is a human cell culture medium comprising ingredients including: a WNT signaling pathway activator; a BMP signaling pathway activator, wherein the ingredients are in sufficient concentration to promote differentiation of a HOXA3+, TBX1+/high, bipotent PPEIII cell to a human a TBX1dim, PAX1+, PAX9+, FOXG1+ ventral PPEIII cell that can further differentiate into the thymus epithelial lineage.

In some embodiments, the medium further comprises human bipotent PPEIII cells.

In some embodiments, the medium further comprises one, some or all of the following: an FGF/ERK/MAPK signaling pathway inhibitor, an IGF signaling pathway activator, and a Sonic Hedgehog (SHH) signaling pathway inhibitor. In some embodiments, the medium comprises an FGF/ERK/MAPK signaling pathway inhibitor. In some embodiments, the medium comprises an IGF signaling pathway activator. In some embodiments, the medium comprises a Sonic Hedgehog (SHH) signaling pathway inhibitor.

Also provided is a human cell culture medium comprising ingredients including: an IFN type I or II signaling pathway activator; an FGF signaling pathway activator; and an IGF signaling pathway activator, wherein the ingredients are in sufficient concentration to promote differentiation of a TBX1dim, PAX1+, PAX9+ FOXG1+ ventral PPEIII cell to a FOXN1+, PSMB11+, EPCAM+ TEPC cell. In some embodiments, the medium further comprises one, some or all of the following: a Sonic Hedgehog (SHH) signaling pathway inhibitor, a canonical WNT signaling pathway inhibitor and a RANKL.

Definitions

"Definitive Endoderm cells," or "DE cells" as used herein, refers to cells which bear the characteristics of cells arising from the epiblast during gastrulation and which form the primitive gut tube and its derivatives. Definitive endoderm cells express at least one of the following markers: FOXA2, SOX17, CXCR4, OTX2, HHEX, CER1, FZD8, GATA6 and SHISA2. A specific marker for DE cells is SOX17. Thus, definitive endoderm cells may be characterized by the expression of SOX17.

"Anterior Foregut cells" or "AFG cells," as used herein, refers to cells derived from definitive endoderm that can give rise to all endodermal organs from the most cranial segment of the primitive gut tube, such as thymus, parathyroid, thyroid, bronchus/lungs, and esophagus. Anterior Foregut cells express at least one of the following markers: SOX2, FOXA2, OTX2, IRX3, IRX5. AFG cells don't express HOXA3. Compared to DE cells, the specific changes of mRNA expression in AFG cells include upregulation of SOX2 and downregulation of SOX17.

"Anterior Foregut-plus cells" or "AFG-plus cells," as used herein, refers to AFG cells that have additionally been treated with dual SMAD inhibition and all-trans retinoic acid (ATRA) at concentrations from 5 nM to 5 uM or another retinoic acid agonist, or a PI3K signaling pathway inhibitor, or an FGF signaling pathway activator or a canonical WNT signaling pathway inhibitor for more than 24 hours. Cell derived in such a fashion are herein referred to as "AFG-plus" cells.

"Bipotent PPEIII cells" as used herein, refers to further specified AFG cells or AFG-plus cells that bear the characteristics of cells branching from the primitive gut tube during organogenesis to form the third pharyngeal pouches with committed differentiation potential to thymus and parathyroid. Bipotent PPEIII cells express at least one of the following markers: HOXA2, HOXA3, TBX1, GATA3. Bipotent PPEIII cells don't express any of the following markers: GATA4, GATA6, SHH, FOXE1, HOXA5, HOXD4, HOXC5, CDX2. Markers specific to bipotent PPEIII cells are coexpression of HOXA3, TBX1 and GATA3. Bipotent PPEIII cells may be characterized by an increase in expression of TBX1 compared to AFG cells. For example, greater than 50 percent of cells in a culture that is collectively deemed to be at the bipotent PPEIII stage typically express TBX1. A four to fifty fold increase in the mRNA expression of TBX1 may be observed in bipotent PPEIII cells compared to AFG cells. Bipotent PPEIII cell with increased TBX1 expression compared to AFG cells are in the following referred to as TBX1+/high.

"Ventral PPEIII cells," as used herein, may be characterized as positive for expression of the following markers: PAX1, PAX9, FOXG1 while their expression of TBX1 is decreased compared to bipotent PPE cells. For example, a greater than tenfold decrease in TBX1 expression may be observed in ventral PPEIII cells compared to the prior stages. Ventral PPEIII cell with reduced TBX1 expression compared to bipotent PPEIII cells are in the following referred to as TBX1dim.

"Ventral PPEIII cells" as used herein, refers to AFG cell- or bipotent PPEIII cell-derivatives capable of becoming thymic epithelial cells. Ventral PPEIII cells bear the characteristics of cells localized to the ventral tip of the third pharyngeal pouches during organogenesis which eventually give rise to thymus tissue containing all subtypes of specialized thymic epithelial cells.

"Dorsal PPEIII cells" as used herein, refers to AFG cell- or bipotent PPEIII cell-derivatives capable of becoming parathyroid epithelial cells. Dorsal PPEIII cells bear the characteristics of cells localized to the dorsal side of the third pharyngeal pouches during organogenesis which connects with the pharynx and eventually gives rise to parathyroid epithelial tissue.

Thymic epithelial progenitor cells" or TEPCs express at least one of the following markers: FOXN1, PSMB 11, EPCAM.

By "bone morphogenic proteins" or "BMPs" it is meant the family of growth factors that is a subfamily of the transforming growth factor 3 (TGF 3) superfamily. BMPs (e.g., BMP1, BMP2, BMP3, BMP4, BMP5. BMP6, BMP7, BMP8a, BMP8b, BMP9/GDF, BMP10, BMP11/GDF11, BMP12/GDF7, BMP13/GDF6, BMP14/GDF5, BMP15/GDF9B) were first discovered by their ability to induce the formation of bone and cartilage. BMPs interact with specific receptors on the cell surface, referred to as bone morphogenetic protein receptors (BMPRs). Signal transduction through BMPRs results in mobilization of members of the SMAD family of proteins, which in turn modulate transcription of target genes. Of particular interest in the present invention arc activators and inhibitors of BMP signaling, which can readily be identified by one of ordinary skill in the art by any of a number of methods, for example competitive binding assays for binding to BMP or BMP receptors, functional assays, e.g., measuring enhancement of activity of downstream signaling proteins such as relocalization of SMADs, such as a BMP-responsive (BR)-SMAD to the nucleus and transcriptional activation/inhibition of downstream gene targets as known in the art.

By "transforming growth factor beta" or "TGFβ" it is meant the TGFβ secreted proteins belonging to the subfamily of the transforming growth factor β(TGFβ) superfamily. TGFβs (TGFβ1, TGFβ2, TGFβ3) are multifunctional peptides that regulate proliferation, differentiation, adhesion, and migration and in many cell types. The mature peptides may be found as homodimers or as heterodimers with other TGFβ family members. TGFβs interact with transforming growth factor beta receptors (TGF-βRs, or TGFβRs) on the cell surface, upon which binding activates MAP kinase-, Akt-, Rho- and Rac/cdc42-directed signal transduction pathways, the reorganization of the cellular architecture and nuclear localization of SMAD proteins, and the modulation of target gene transcription. Further inhibitors of TGFβ signaling, which can readily be identified by one of ordinary skill in the art by any of a number of methods, for example competitive binding assays for the binding to TGFβ or TGFβ receptors, or functional assays, e.g., measuring suppression of activity of downstream signaling proteins such as MAPK, Akt, Rho, Rac, and SMADs, e.g., Activin-responsive (AR)-SMAD, etc., as known in the art.

"WNT" refers to the family of highly conserved secreted signaling molecules that play key roles in both embryogenesis and mature tissues. The human WNT gene family has at least 19 members (WNT-1, WNT-2, WNT-2B/WNT-13, WNT-3, WNT3a, WNT-4, WNT-5A, WNT-5B, WNT-6, WNT-7A, WNT-7B, WNT-8A, WNT-8B, WNT-9A/WNT-14, WNT-9B/WNT-15, WNT-10A, WNT-10B, WNT-11, WNT-16). WNT proteins modulate cell activity by binding to WNT receptor complexes that include a polypeptide from the Frizzled (Fz) family of proteins and a polypeptide of the low-density lipoprotein receptor (LDLR)-related protein (LRP) family of proteins. Once activated by WNT binding, the WNT receptor complex will activate one or more intra-cellular signaling cascades. These include the canonical WNT signaling pathway; the WNT/planar cell polarity (WNT/PCP) pathway; and the WNT-calcium (WNT/Ca2+) pathway. The WNT pathway can be classified broadly as canonical and non-canonical. Both pathways are activated by a WNT ligand to the Frizzled receptor. The active canonical pathway is mediated by 0-catenin, which translocates into the nucleus where it acts as a co-activator of the TCF/LEF transcription factor, leading to the upregulation of WNT target genes. The two major non-canonical pathways are WNT/calcium and Planar Cell Polarity (PCP) pathways. In the WNT/calcium pathway, WNT binding to Frizzled activates Dv1, which stimulates calcium release from the endoplasmic reticulum, activating calcium-binding proteins including protein kinase C (PKC) and calmodulin-dependent kinase II (CaMKII), and in turn, the transcription factor NFAT. The WNT/calcium pathway has been shown to regulate cell movement and axis formation during embryogenesis. The WNT/PCP pathway is mediated by the GTPases RhoA and Ras, which, via the activation of the RhoA-Rho-associated kinase (ROCK) axis or JNK, can exert effects on the cytoskeleton.

The terms “treatment”, “treating” and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. “Treatment” as used herein covers any treatment of a disease in a mammal and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms “individual”, “subject”, “host”, and “patient” are used interchangeably herein and refer to any mammalian subject for whom diagnosis, treatment, or therapy is desired, particularly in humans.

The term “medium” in the context of cell culture or the phrase “cell culture medium” or “cell medium” refers to a cellular growth medium suitable for culturing of pluripotent stem cells (PSCs), DE cells, AFG cells, AFG-plus cells, bipotent PPEIII cells, ventral PPEIII cells, and TEPCs. Examples of cell culture medium include, without limitation to, Minimum Essential Medium (MEM), Dulbecco’s Modified Eagle Medium (DMEM), Dulbecco’s Modified Eagle Medium: Nutrient Mixture F-12 (DMEM/F12), Ham’s F10 Nutrient Mixture, Ham’s F12 Nutrient Mixture, Medium 199, RPMI, RPMI 1640, reduced serum medium, Basal Medium Eagle’s (BME), and the like, and combinations thereof. The medium or cell culture medium may be modified by adding one or more additives. Additives may include serum, such as, fetal bovine serum and/or serum replacement agents, such as, B27, N2, KOSR, and combinations thereof, and differentiation factors as described herein.

BRIEF DESCRIPTION OF THE DRAWINGS

FIG. 6A-B: 6A illustrates the capacity of bipotent PPEIII cells to give rise to both, ventral PPEIII cells and subsequently TEPCs, as well as dorsal PPEIII cells and subsequently parathyroid epithelial precursor cells (PEPCs) when directed with the appropriate signals. (6B) Expression levels of the TEC/TEPC maker FOXN1 across different primary and iPSC-derived tissues relative to the housekeeping gene GAPDH. Expression levels of the parathyroid and PEPC maker GCM2 across different iPSC-derived tissues relative to the housekeeping gene GAPDH.

DETAILED DESCRIPTION OF THE INVENTION

The inventors have discovered an in vitro differentiation platform for the efficient generation of TEPCs from human pluripotent stem cells (PSC) by recapitulating the sequential stages of human thymic ontogeny: Definitive Endoderm (DE), Anterior Foregut (AFG), Bipotent Third Pharyngeal Pouch Endoderm (bipotent PPEIII), Ventral Third Pharyngeal Pouch Endoderm (ventral PPEIII) and Thymic Epithelial Progenitor Cells (TEPC). These TEPCs can further mature into functional cTECs and mTECs either in vivo after transplantation or in vitro through further signal induction. Accordingly, methods of differentiating cells into any of these intermediate stages or into bipotent PPEIII cells, ventral PPEIII cells or TEPCs are provided, starting from any cell type that can be differentiated into DE cells or AFG cells.

Figure 1:
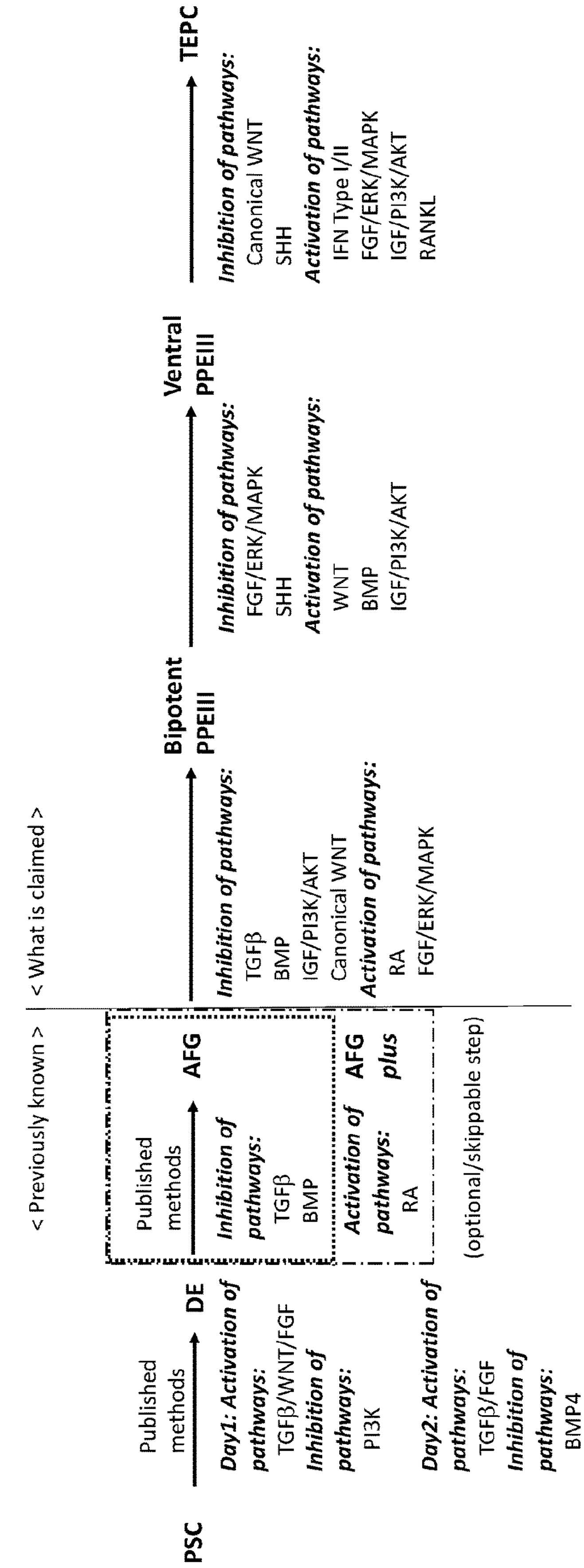
FIG. 1 Overview of the 5 step TEPC differentiation protocol using human pluripotent stem cells (PSC). Activating and inhibiting signals are detailed.

The process of differentiating pluripotent stem cells into functional TEPCs in vitro may be viewed as progressing through five consecutive stages, as is shown in the exemplary protocol depicted in FIG. 1 In this stepwise progression, "Stage 1" refers to the first step in the differentiation process, the differentiation of PSC into cells expressing markers characteristic of DE cells. "Stage 2" refers to the second step, the differentiation of cells expressing markers characteristic of DE cells into cells expressing markers characteristic of AFG cells. "Stage 3" refers to the third step, the differentiation of cells expressing markers characteristic of AFG cells into cells expressing markers characteristic of bipotent PPEIII cells. "Bipotent" as used herein refers to the ability of Stage 3 cells to differentiate into thymus or parathyroid. "Stage 4" refers to the fourth step, the differentiation of cells expressing markers characteristic of bipotent PPEIII cells into cells expressing markers of ventral PPEIII cells. "Stage 5" refers to the fifth step, the differentiation of cells expressing markers characteristic of ventral PPIII cells into cells expressing markers characteristic of TEPCs. Not all cells in a particular population progress through these stages at the same rate, i.e., some cells may have progressed less, or more, down the differentiation pathway than the majority of cells present in the population.

In some embodiments, the methods begin with DE cells. Optionally DE cells can be generated from any cell that can be differentiated into a DE cell. Any human pluripotent cells can be used including but not limited to human embryonic stem cells (hESCs), human induced pluripotent stem cells (hiPSCs) or human embryonic germ cells (hEGCs). In some cases, human adult stem cells or progenitors may be used to induce TEPCs with the methods and medium composition disclosed herein.

Methods of generating DE are known and include but are not limited to Loh et al (Loh, Ang et al., 2014 *Cell Stem Cell*). The method of Loh et al can be used or adapted to generate DE cells from human PSCs. Other methods to generate DE cells, are also suitable.

In some embodiments, the methods begin with AFG cells. Optionally, AFG cells can be generated from any cell that can be differentiated into a AFG cell. Methods of making AFG cells are known and include but are not limited to Green et al. (Green, Chen et al. 2011 *Nature Biotechnology*). The method of Green et al can be used or adapted to generate AFG cells from DE cells. Other methods to generate AFG cells, are also suitable.

In some embodiments, the methods to differentiate bipotent PPEIII cells can start with AFG cells that have additionally been treated with dual SMAD inhibition and all-trans retinoic acid (ATRA) at concentrations from 5 nM to 5 uM or another retinoic acid agonist, or a PI3K signaling pathway inhibitor, or an FGF signaling pathway activator or a canonical WNT signaling pathway inhibitor for more than 24 hours. Cell derived in such a fashion are herein referred to as "AFG-plus" cells.

In some embodiments, either DE cells or AFG cells or AFG-plus cell can be used as starting material to generate bipotent PPEIII cells.

Basal medium can be, without limitation, chemically defined medium (CDM2), RPMI1640 or DMEM/F12. Basal medium can be supplemented with, but not limit to, Knockout serum replacement (KOSR), B27 or N2 supplements. This medium composition applies to all the stages of the TEPC differentiation methods. Other basal media with different bases as defined above can be used.

As demonstrated in the Examples and FIG. 1, DE or AFG or AFG-plus cells can be used as starting material for the methods of making bipotent PPEIII cells. The additional treatment of DE cell with dual SMAD inhibition or of AFG cells with any additional factors is not required as a starting material to induce the bipotent PPEIII stage. Bipotent PPEIII cells are biologically defined by their dual capacity to give rise to thymus and parathyroid. These cells are HOXA3+/high, TBX1+/high, wherein "high" is defined as respective expression levels of HOXA3 and TBX1 peaking at the bipotent PPEIII stage after which HOXA3 and TBX1 expression will decline as detailed above. The resulting cells have a committed fate to PPEIII and have the potency to further differentiate into thymus/parathyroid epithelial lineages. To achieve these bipotent PPEIII cells, DE cells or AFG cells or AFG-plus cells were cultured in basal medium, e.g., as described above, that further comprises a Transforming Growth Factor (TGFβ) signaling pathway inhibitor (e.g., A 83-01 at 1 nM-10 uM); a Bone Morphogenic Protein (BMP) signaling pathway inhibitor (e.g., LDN193189 at 1 nM-10 uM); a retinoic acid (RA) signaling pathway activator (e.g., ATRA at 5 nM-5 uM); and a PI3K/AKT signaling pathway inhibitor (e.g., PI 828 at 0.05 uM-50 uM). The inventors have found that the induction of the bipotent PPEIII stage is further enhanced by addition of one or more of a Fibroblast Growth Factor (FGF) signaling pathway activators (e.g., FGF7 and/or FGF10, at least 1 ng/ml) or a canonical WNT signaling pathway inhibitor (e.g., IWR-1 at 5 nM to 5 uM) or both to the medium to further improve conversion to bipotent PPEIII cells.

Exemplary TGFβ signaling pathway inhibitors include, without limitation, an ALK5 inhibitor including A 83-01, LY364947, LY580276, SB505124, SB431524, SB525334, SM16, SD208. D4476, GW6604, GW788388, TP0427736, BIBF-0775, CAS 446859-33-2, or an anti-TGFβ antibody including Vactosertib.

Exemplary BMP signaling pathway inhibitors include, without limitation, an ALK2 inhibitor or ALK3 inhibitor e.g., LDN193189, Noggin, DMH2, K02288, ML374, LDN214117, DMH-1, LDN212854, or Dorsomorphin dihydrochloride.

Exemplary retinoic acid (RA) signaling pathway activators include reagents which activates any retinoic acid receptor (RAR α/β/γ and RXR), and wherein the RAR activator include, without limitation, all-trans retinoic acid (ATRA), and analogs of ATRA including TTNPB, Tamibarotene, BMS-189453, CD1530, Adapalene, Tazarotenic acid, CD437, BMS753, CD2314, BMS961, CH55, AM580, AM80, AC55649, AC261066, EC19, BMS493, DC271, or EC23. RXR activators include, without limitation, SRI1237 and 9-cis-Retinoic Acid.

Exemplary PI3K/AKT signaling pathway inhibitors include reagents that can inhibit the signal at any level of this pathway including IGF receptors, PI3K(α/β/δ/γ), AKT (AKT1/2/3) and their substrates. Some examples include, without limitation, PI 828 (0.05 uM-50 uM), LY294002, PI 103, GSK1059615, ETP45658, API-1, API-2, GSK690693, GSK1904529A, GDC-0941, PIK90, TGX-221, IC-87114, BKM120, BEZ235, and GS-1101.

Exemplary FGF signaling pathway activators include, without limitation, FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, and FGF22.

Exemplary canonical WNT signal inhibitors include, without limitation, endo-IWR 1 (5 nM-5 uM), IWP2, XAV939, JW55, SM04690, LF3, WIK14, G007-LK and G244-LM.

The duration of bipotent PPEIII induction under the aforementioned regimes can take, for example, 2 to 14 days, depending on the concentration of each individual reagent used, to reach the inductive dosage for PPEIII differentiation.

Accordingly, in some embodiments, a culture of cells is provided that is enriched for HOXA3+, TBX1+/high, bipotent PPEIII cells. For example, in some embodiments, the culture comprises at least 50, 60, 70, 80, 90, 95, or 99% HOXA3+, TBX1+/high, bipotent PPEIII cells. The cell cultures can be made for example using the methods described herein.

The present inventors have also discovered signals that work synergistically to specify bipotent PPEIII cells towards thymic fate. For example, one can culture a bipotent PPEIII cell into a ventral PPEIII cell, i.e., a TBX1dim, PAX1+, PAX9+, FOXG1+ cell that can further differentiate into a TEPC. For example, bipotent PPEIII cells can be cultured in a medium that activates WNT and BMP signals together, optionally with one or some or all of the following: FGF/ERK/MAPK signaling pathway inhibitor, an IGF signaling pathway activator, and a Sonic Hedgehog (SHH) signaling pathway inhibitor.

In some embodiments, the culture medium comprises a WNT activator and a BMP activator. In some embodiments, the culture medium comprises a WNT activator and a BMP activator and a SHH inhibitor. In some embodiments, the culture medium comprises a WNT activator and a BMP activator and an FGF/ERK/MAPK inhibitor. In some embodiments, the culture medium comprises a WNT activator and a BMP activator and an IGF/PI3K/AKT activator. In some embodiments, the culture medium comprises a WNT activator and a BMP activator and an FGF/ERK/MAPK inhibitor and an IGF/PI3K/AKT activator. In some embodiments, the culture medium comprises a WNT activator and a BMP activator and an FGF/ERK/MAPK inhibitor and a SHH inhibitor. In some embodiments, the culture medium comprises a WNT activator and a BMP activator and an FGF/ERK/MAPK inhibitor and an IGF/PI3K/AKT activator and a SHH inhibitor.

WNT signal activation can be achieved, for example, by WNT proteins and/or small molecule agonists targeting the WNT pathway. CHIR99021 (1 nM-10 uM) is in some embodiments used as a reagent in this regime for WNT activation, which works as a potent canonical WNT agonist by targeting GSK3b. Canonical WNT signal family members such as WNT3a (at least 1 ng/ml) works as alternative to activate WNT signaling. Noncanonical WNT proteins can be used in combination with canonical WNT proteins. In addition, R-spondin (RSOP) reagents can be used in combination with WNT proteins to enhance WNT signal activation. Canonical and noncanonical WNT proteins include, without limitation, WNT1, WNT2, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16. Small molecule WNT activators include, without limitation, CHIR99021, LiCL, WAY-316606, ABC99, IQ1, QS 11, SB-216763, BIO(6-bromoindirubin-3'-oxime), LY2090314, DCA, 2-amino-4-13,4-(methylenedioxy) benzyl-amino]-6-(3-methoxyphenyl) pyrimidine.

BMP signal activation is achieved by BMP4 (at least 1 ng/ml). Other BMP family members can be added in the regime together with BMP4 or replace BMP4. These BMP family members include, without limitation, BMP1, BMP2, BMP3, BMP5, BMP6, BMP7, BMP8a, BMP8b, BMP9, BMP10, BMP11, BMP12, BMP13.

Exemplary FGF/ERK/MAPK signaling pathway inhibitors can include inhibitors at the various levels of the pathway, e.g., a FGF receptor antagonist including, without limitation, SU 5402 (1 nM-10 uM), SU6668, PD161570, PD166285, PD173073; a MAPK inhibitor including, without limitation, U0126 (5 nM-50 uM), PD98059; an ERK inhibitor including, without limitation, SCH772984, FR180204 and TCS ERK11e.

Exemplary IGF/PI3K/AKT signaling pathway activators include, without limitation, IGF-1 (at least 0.1 ng/ml), IGF-2 (at least 1 ng/ml) and insulin.

Exemplary SHH signaling pathway inhibitors include, without limitation, Vismodegib (0.1 nM-1 uM), XL-139 (0.1 nM-1 uM), GANT61, MK-4101, HPI-4, Jervine, cyclopamine, PF-5274857, JK184, LY2940680 or Sonidegib. SHH agonizing and antagonizing signals can drive cell fate in such bipotent PPEIII cells further towards thymus and parathyroid fate respectively. Exemplary SHH signaling pathway activators driving further differentiation towards parathyroid include, without limitation, SAG (0.1 nM-1 uM) or SAG 21k (0.1 nM-1 uM).

The duration of induction of bipotent PPEIII cells into TBX1dim, PAX1+, PAX9+, FOXG1+ ventral PPEIII cells under the aforementioned regime can be for example 3-5 days. In some cases, it can take 1 to 10 days, depending on the concentration of each individual reagent used and the responsiveness of different samples.

Accordingly, in some embodiments, a culture of cells is provided that is enriched forTBX1dim, PAX1+, PAX9+, FOXG1+ ventral PPEIII cells. For example, in some embodiments, the culture comprises at least 50, 60, 70, 80, 90, 95, or 99% TBX1dim, PAX1+, PAX9+, FOXG1+ ventral PPEIII cells. The cell cultures can be made for example using the methods described herein.

The present inventors have also discovered one can culture and differentiate a TBX1dim, PAX1+, PAX9+, FOXG1+ ventral PPEIII cell to a TEPC (e.g., FOXN1+, PSMB11+, EPCAM+). A TEPC can further mature into functional cTECs and mTECs either in vivo after transplantation or in vitro through further signal induction. cTECs are mature TECs and can further differentiate to AIRE+ mTEC lineage cells. To generate TEPCs, ventral PPEIII cells can be cultured in a medium that contains one, some or all of the followings: IFN type I and/or II signaling activators, FGF signaling pathway activators, and IGF signaling pathway activators, optionally with inhibition of SHH signaling pathways and/or inhibition of the canonical WNT signaling pathway In some embodiments, the culture medium comprises an IFN type I and/or II signal activator and a FGF signal activator and an IGF signal activator. In some embodiments, the culture medium comprises an IFN type I and/or II signal activator and a FGF signal activator and an IGF signal activator and a SHH signal inhibitor. In some embodiments, the culture medium comprises an IFN type I and/or II signal activator and a FGF signal activator and an IGF signal activator and a canonical WNT signal inhibitor. In some embodiments, the culture medium comprises an IFN type I and/or II signal activator and a FGF signal activator and an IGF signal activator and a SHH signal inhibitor and a canonical WNT signal inhibitor.

IGF signaling pathway activators, SHH signaling pathway inhibitors, FGF signaling pathway activators, and canonical WNT signaling pathway inhibitors can be selected as described above.

IFN type I and/or II signal activation can be achieved with, without limitation, IFN-alpha (at least 1 U/ml), IFN-beta (at least 1 pg/ml), IFN-gamma (at least 0.05 ng/ml).

Accordingly, in some embodiments, a culture of cells is provided that is enriched for FOXN1+, PSMB11+, EPCAM+ TEPCs. For example, in some embodiments, the culture comprises at least 10, 20, 30, 40, 50, 60, 70, 80, 90, 95, or 99% FOXN1+, PSMB11+, EPCAM+ TEPC cells. The cell cultures can be made for example using the methods described herein.

In some embodiments, one can combine the above methods, for example to start with DE or AFG or AFG-plus cells, differentiate them into bipotent PPEIII cells, which in turn can optionally be differentiated into ventral PPEIII cells and optionally subsequently into TEPC cells.

Any of the cells made as described herein, e.g., HOXA3+, TBX1+/high, bipotent PPEIII cells: TBX1 dim, PAX1+, PAX9+, FOXG1+ ventral PPEIII cells: or FOXN1+, PSMB11+, EPCAM+ TEPC cells can be administered to a human, for example to treat a disorder. In some embodiments the cells are derived from the individual human, differentiated by one or more of the methods described herein and introduced to the same individual. In this case the cells are termed "autologous". In other embodiments, cells from one or more individuals are differentiated by one or more of the methods described herein and introduced into a different individual. In this case, the cells are termed "allogeneic." For allogenic transplantation, in some embodiments, the cells will be partly or fully HLA-matched to the individual.

Optionally, the cells can be genetically modified before introduction into an individual. For example, in embodiments in which the recipient has a defective gene, the cells can be modified to have a wildtype copy of the relevant gene, and then can be introduced into the individual. Any method available can be used to modify the cells. For example, in some embodiments, a targeted nuclease introduces a double-stranded break at a target site in a chromosome of the cells and homology directed repair (HDR) is used in the presence of a polynucleotide that is introduced into the double-stranded break. In some embodiments, for example, the targeted nuclease is selected from the group consisting of an RNA-guided nuclease domain, a transcription activator-like effector nuclease (TALEN), a zinc finger nuclease (ZFN) and a megaTAL. In some embodiments, CRISPR/Cas9 or other CRISPR methods are used to target and introduce the double-stranded break and introduce the polynucleotide into the cell.

The cells described herein can be used to ameliorate, for example, any diseases or disorders involving defective thymic epithelial cells. Exemplary individuals receiving the cells can include, for example, individuals born with congenital thymic aplasia, due to 22q11 Deletion Syndrome, or mutations in TBX1, FOXN1 or CHD7, for example who can present with T-cell immunodeficiency. In other embodiments, the cells described herein can be administered to human patients before or during or after hematopoietic stem cell transplantation (HSCT), for example to mitigate the injury caused to thymic cells by acute graft-versus-host disease (aGVHD). In other embodiments, the cells described herein can be administered to individuals having compromised thymic function, for example but not limited to, caused by infection, cancer, irradiation, medication or iatrogenic surgical removal due to cardiac surgeries. In other embodiments, the cells described herein can be administered to elderly individuals, e.g., over 50, 55, 60, 65, 70, 75, or 80 years old, for example individuals experiencing reduced thymic function due to age (immune senescence).

In some embodiments, the cells as described herein can be used to induce tolerance to transplanted solid organs (for example but not limited to kidney, heart, lung, islet cells or liver). In some embodiments, autologous or HLA-matched allogeneic cells as described herein are used to induce stable donor-specific immune tolerance during allogeneic solid organ transplant. This can reduce the dependence of patients on immunosuppressive drugs and address the current shortage of HLA-matched donor organs.

In some embodiments, the cells as described herein can be administered to a recipient of pancreatic islet (β-cells) to treat type I diabetes mellitus (DM). Thymic dysfunction contributes to the development of type I DM through impaired presentation of tissue-restricted antigens and/or negative selection of autoreactive T cells, thus is permissive of the production of self-reactive T cells that target and destroy islet cells. The thymic transplant can eliminate these self-reactive T cells through negative selection (clonal deletion) of autoreactive T cells on AIRE-positive thymic epithelial cells that express tissue restricted antigens (including pro-insulin) and through the generation of regulatory T cells to further protect islet function through induction of central tolerance.

In some embodiments, the cells as described herein can be cultured in a bioreactor. Optionally, the bioreactor further comprises T-cells, which can be amplified. This approach, for example, can be used to enable highly efficient in vitro T cell production for any T cell editing/engineering purpose and solves the limitations in T cell generation for any type of T cell therapies.

In some embodiments, the cells as described herein can be formed into organoids or synthetic organs. In some embodiments, 3D thymic organoids are formed by coculturing in vitro derived TEPCs with mesenchymal cells in a synthetic matrix. Exemplary matrices include but are not limited to hydrogels containing elastin-like protein (ELP) and hyaluronic acid. These 3D thymic organoids can be used in any of the aforementioned applications in place of TEPCs generated in 2D monolayer cultures. Mesenchymal cells can be primary cells derived from human thymic tissues or differentiated in vitro from pluripotent stem cells.

EXAMPLES

The outline of the stepwise differentiation protocol to thymic epithelial progenitor cells using human pluripotent stem cells is illustrated in FIG. 1. The entire course of in vitro differentiation can be divided into 5 stages based on the phenotype of the differentiated cells achieved at each stage under corresponding inductive signals:

Stage 1: generation of DE cells from human pluripotent stem cells

Stage 2: generation of AFG or AFG-plus cells from DE cells

Stage 3: generation of bipotent PPEIII cells from AFG cells

Stage 4: generation of ventral PPEIII cells from bipotent PPEIII cells

Stage 5: generation of thymic epithelial progenitor cells (TEPCs) from ventral PPEIII cells In vitro differentiation stage 1: generation of DE cells from human pluripotent stem cells.

Figure 2:
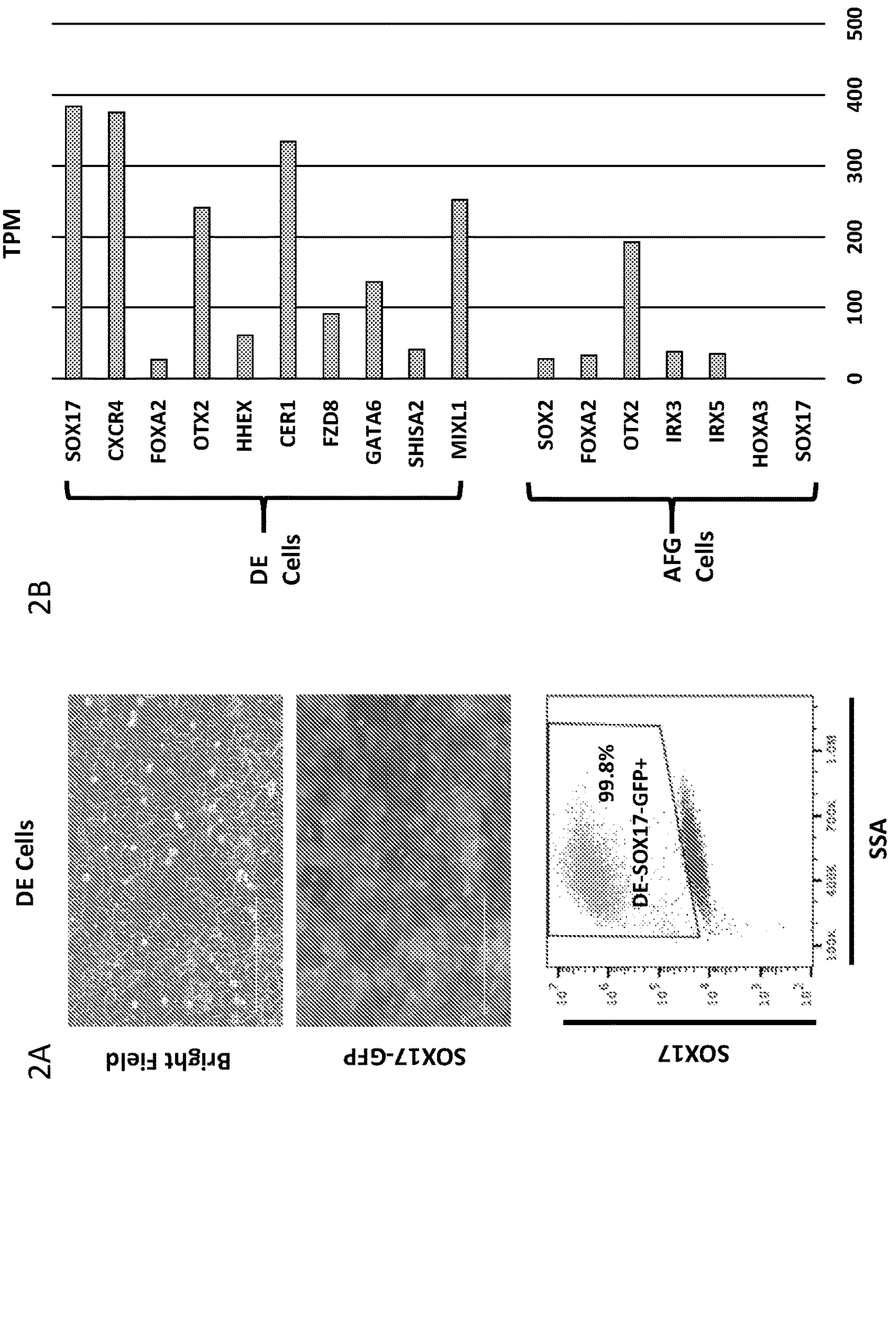
FIG. 2 (A-B) shows the induction of DE and AFG. Homogenous expression of SOX17 in DE with <1% SOX17 negative cells. (B) Expression of Stage-specific markers in DE and AFG respectively are confirmed by Taqman qRT-PCR.

The method to generate DE cells is adapted from the work of Loh (Loh, Ang et al, 2014*, Cell Stem Cell*). As shown in FIG. 2, such DE cells express endodermal markers such as SOX17, CXCR4, and FOXA2 in nearly 100% of the population (FIG. 2A).

In vitro differentiation stage 2: generation of AFG or AFG-plus cells from DE cells The method of AFG generation provided in this present patent is based on inhibition of both TGFβ and BMP signaling pathways (a.k.a, dual SMAD inhibition). Dual SMAD inhibition was first reported by Green et al (Green, Chen et al. 2011 *Nature Biotechnology*) to induce AFG cells.

Figure 3:
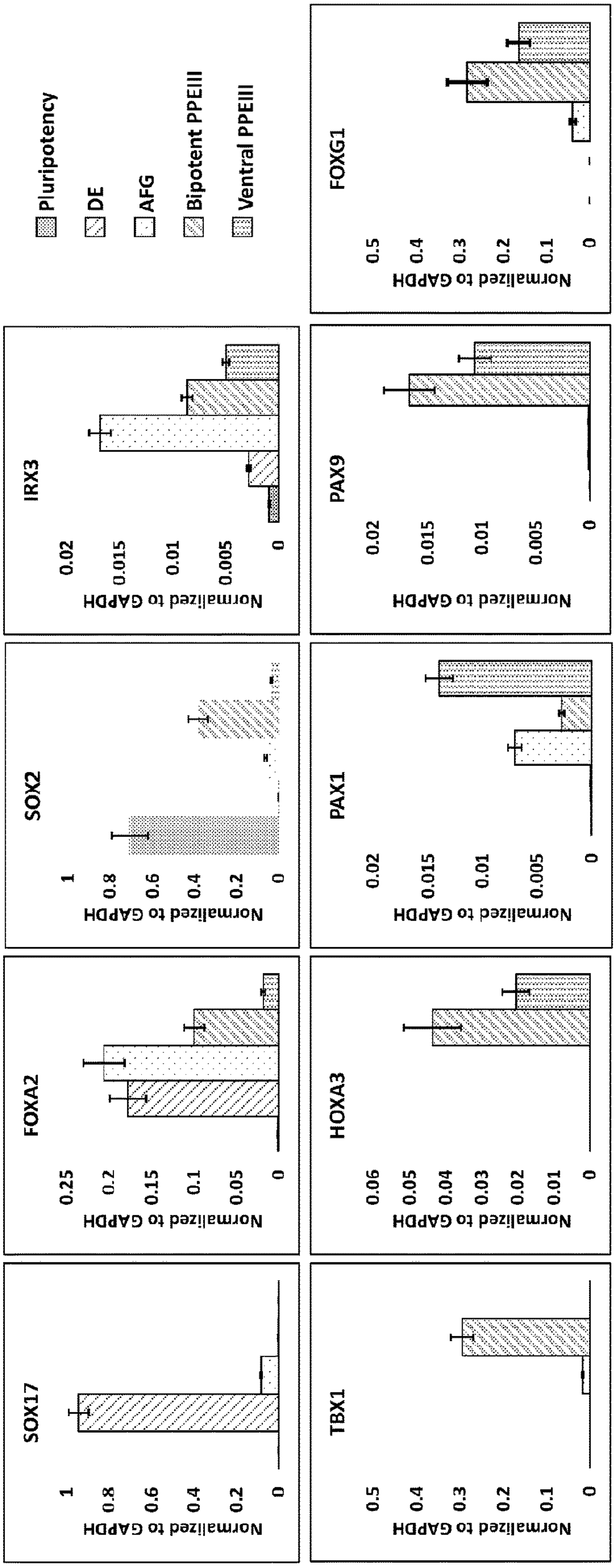
FIG. 3 illustrates the changes in expression levels of key developmental markers across the 6 stages of thymic epithelial development from pluripotency, DE. AFG, bipotent PPEIII, ventral PPEIII to TEPC fate. mRNA expression levels of individual markers are represented relative to the mRNA expression level of the housekeeping gene GAPDH.
Figure 4:
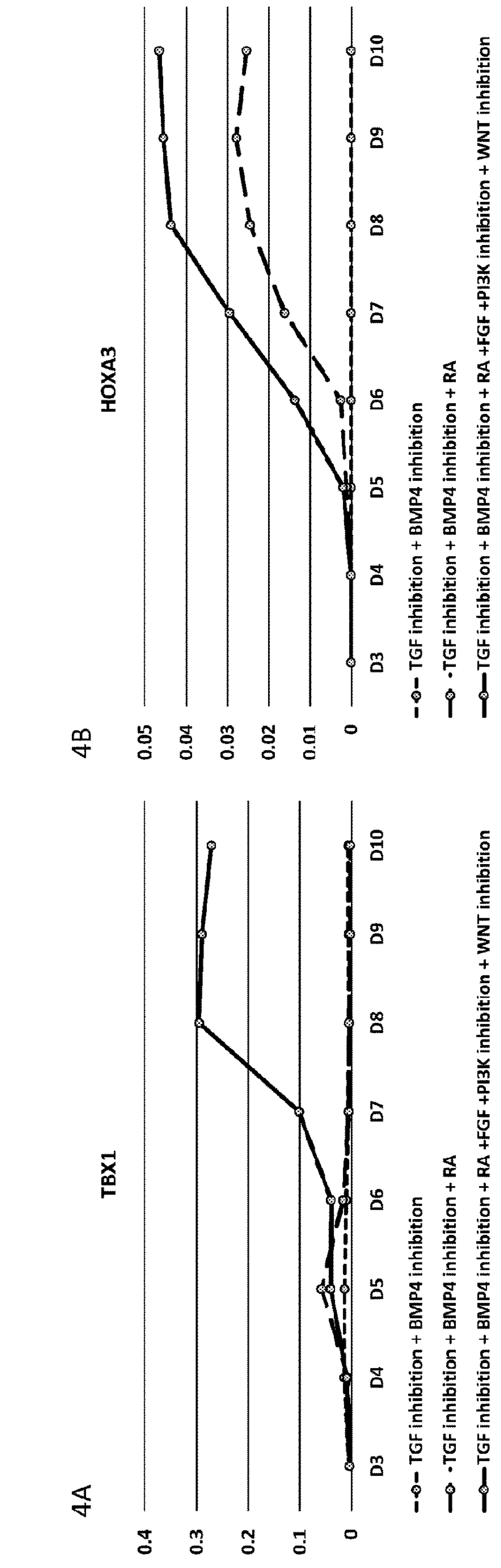
FIG. 4A-B illustrates the differentiation of AFG to bipotent PPEIII under the combined induction of multiple signals. (4A) dynamic temporal changes of TBX1 mRNA expression 1) with TGF inhibition and BMP4 inhibition alone, 2) with TGF inhibition and BMP4 inhibition in conjunction with retinoic acid (RA), 3) with TGF inhibition and BMP4 inhibition in conjunction with RA, FGF, P13K inhibition and Canonical WNT inhibition. (4B) dynamic temporal changes of HOXA3 mRNA expression 1) with TGF inhibition and BMP4 inhibition alone, 2) with TGF inhibition and BMP4 inhibition in conjunction with retinoic acid (RA), 3) with TGF inhibition and BMP4 inhibition in conjunction with RA, FGF, PI3K inhibition and Canonical WNT inhibition. mRNA expression levels of individual markers are represented relative to the mRNA expression level of the housekeeping gene GAPDH.
Figure 5:
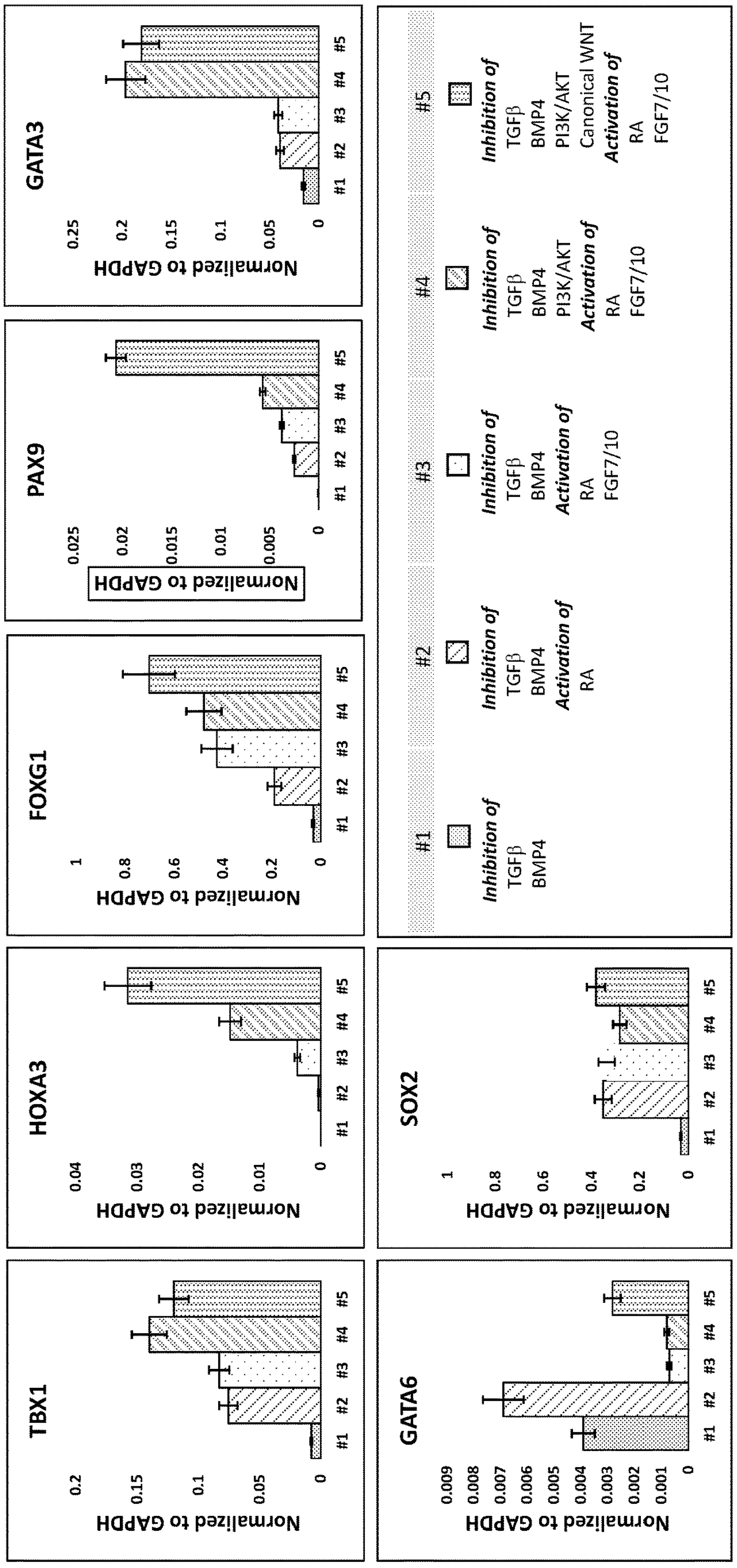
FIG. 5 details the expression levels of key markers of the bipotent PPEIII stage (TBX1, HOXA3, FOXG1, PAX9, GATA3, GATA6 and SOX2) in response to different combinations of inductive signals which in their collectiveness (#5) constitute the methods claimed herein to differentiate a suitable precursor population (DE cell, AFG cells, AFG-plus cells) into bipotent PPEIII cells.

In the disclosed method, DE cells were cultured in basal medium containing dual SMAD inhibition reagents to induce AFG cells with or without low concentrations of ATRA for 2 days. For example, TGFβ signal inhibitor A 83-01 (1 uM) combined with BMP signal inhibitor LDN193189 (250 nM), can specify DE cells into AFG cells that express SOX2, FOXA2 and OTX2 (FIG. 2B). Optional addition of ATRA (5 nM-5 uM) can induce AFG-plus cells In vitro differentiation stage 3: generation of bipotent PPEIII cells from AFG or AFG-plus cells The present invention provided a novel approach to advance AFG or AFG-plus cells to bipotent PPEIII cells. As shown in FIGS. 4 and 5, continued dual SMAD inhibition together with PI3K/AKT pathway inhibition (e.g., PI 828 at 5 uM) plus canonical WNT signal inhibition (e.g., endo-1WR 1 at 250 nM) plus FGF/ERK/MAPK pathway activation (e.g., FGF 7 at 20 ng/ml and FGF10 at 20 ng/ml) and optimal ATRA signal activation (e.g., ATRA at 50-100 nM) for 3-7 days drives AFG or AFG-plus cells into bipotent PPEIII cell stage. Compared to AFG or AFG-plus cells, the expression of TBX1, HOXA3 and PAX9 in bipotent PPEIII cells is significantly increased while GATA4 and GATA6 expression is significantly decreased which inhibits the differentiation bifurcating to liver and lung development respectively. The highly controlled modulation of RA in combination of the aforementioned signals is necessary to achieve the synchronized expression of the bipotent PPEIII markers (HOXA3, PAX9, FOXG1 and TBX1), which are detected in >95% of cells in our bipotent PPEIII protocol. Notably, the RA treatment dosage in the experiments in FIG. 5 throughout conditions #3 through #5 was lower than what was used in FIGS. 3 and 4 which accounts for the overall lower absolute expression levels for TBX1 and HOXA3 in this set of experiments.

In vitro differentiation stage 4: generation of ventral PPEIII cells from bipotent PPEIII cells Bipotent PPEIII cells are biologically defined by their dual capacity to give rise to thymus and parathyroid. The present inventors discovered critical signals that work synergistically to specify bipotent PPEIII cells towards thymic fate through ventral PPEIII stage. As shown in FIG. 3, TBX1dim, PAX1+, PAX9+, FOXG1+ ventral PPEIII cells were generated through combined activation of WNT signal (e.g., CHIR99021 at 2 uM). BMP signal (e.g., BMP4 at 10 ng/ml) and IGF signal (e.g., IGF2 at 10 ng/ml) together with FGF/ERK/MAPK signal inhibition (e.g., U0126 at 10 uM), and SHH signal inhibition (e.g., Vismodegib at 200 nM) for 5 days.

Dynamic downregulation of TBX1 was observed in ventral PPEIII cells under the aforementioned differentiation regime, while upregulation in GCM2 and persistent TBX1 expression remained in cells committed to parathyroid fate under SHH signal activation (FIG. 6).

In vitro differentiation stage 5: generation of TEPCs from ventral PPEIII cells

The present inventors discovered signals further driving the maturation of ventral PPEIII cells into TEPCs, which include at least an IFN type I or II signaling pathway activator: an FGF signaling pathway activator: and an IGF signaling pathway activator. Under the induction of IFN-alpha (1 U/ml), IFN-gamma (0.05 ng/ml), FGF7 and FGF10 (10 ng/ml), and IGF2 (20 ng/ml) for 5 days, the results in FIG. 6 showed the level of FOXN1 expression in the TEPCs differentiated under the aforementioned regime reached approximately 20% of the level found in purified human fetal thymic epithelial cells (EPCAM+ selected by MACS sorting).

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of differentiating a Definitive Endoderm (DE) cell or Anterior Foregut (AFG) cell or an Anterior Foregut (AFG) plus cell to a HOXA3+, TBX1+/high, bipotent PPEIII cell that has a committed fate to PPEIII and has the potency to further differentiate into thymus and parathyroid epithelial lineages, the method comprising culturing the DE cell or AFG cell or AFG plus cell in a medium comprising at least:

a Transforming Growth Factor (TGF-β) signaling pathway inhibitor;

a Bone Morphogenic Protein (BMP) signaling pathway inhibitor;

a Retinoic Acid (RA) signaling pathway activator;

a PI3K/AKT signaling pathway inhibitor; and a Fibroblast Growth Factor (FGF) signaling pathway activator, wherein the culturing of the DE or AFG or AFG-plus cell promotes differentiation to a bipotent PPEIII cell specified for PPEIII and primed for thymus or parathyroid fate.

2. The method of claim 1, wherein the medium further comprises a canonical WNT signaling pathway inhibitor.

3. The method of claim 1, further comprising differentiating the HOXA3+, TBX1+/high bipotent PPEIII cell into a human TBX1dim, PAX1+, PAX9+, FOXG1+ ventral PPEIII cell by:

culturing the bipotent PPEIII cell in a second medium comprising:

a WNT signaling pathway activator;

a BMP signaling pathway activator;

an IGF signaling pathway activator; and a Sonic Hedgehog (SHH) signaling pathway inhibitor, wherein the culturing promotes differentiation of the bipotent PPEIII cell to a ventral PPEIII cell.

4. The method of claim 3, further comprising differentiating the ventral PPEIII cell to a FOXN1+, PSMB11+, EPCAM+thymic epithelial progenitor cell (TEPC) by culturing the ventral PPEIII cell in a third medium comprising:

an IFN type I or II signaling pathway activator;

a FGF signaling pathway activator; and
an IGF signaling pathway activator.

5. The method of claim 4, wherein the third medium further comprises one, both or all three of the following: a Sonic Hedgehog (SHH) signaling pathway inhibitor, a canonical WNT signaling pathway inhibitor and a RANK ligand.

6. The method of claim 1, wherein the DE or AFG cell is a primary DE or AFG cell, respectively.

7. The method of claim 1, wherein the method comprises obtaining the DE cell or AFG cell from a human.

8. The method of claim 4, wherein the method further comprises introducing the TEPC into a human.

9. The method of claim 8, wherein the TEPC is autologous to the human individual.

10. The method of claim 8, wherein the TEPC is allogenic to the human individual.

11. The method of claim 8, wherein the human has congenital thymic aplasia (congenital athymia), thymic injury, reduced thymic function (e.g., due to HSCT status, aGVHD, infection, tumor, irradiation, medications or iatrogenic surgical removal due to cardiac surgeries), or age-related decline in thymic function.

12. A method of differentiating a HOXA3+, TBX1+/high, bipotent PPEIII cell to a human TBX1dim, PAX1+, PAX9+, FOXG1+ventral PPEIII cell that can further differentiate into thymic epithelial progenitor cells, the method comprising culturing the bipotent PPEIII cell in a medium comprising at least:

a WNT signaling pathway activator;
a BMP signaling pathway activator;
an IGF signaling pathway activator; and
a Sonic Hedgehog (SHH) signaling pathway inhibitor,
wherein the culturing promotes differentiation of the bipotent PPEIII cell to a ventral PPEIII cell, and
wherein the WNT signaling pathway activator is a non-canonical WNT signaling pathway activator and/or the IGF signaling pathway activator is IGF2.

13. The method of claim 12, wherein the method further comprises introducing the ventral PPEIII cell into a human.

14. A method of differentiating a TBX1dim, PAX1+, PAX9+, FOXG1+ventral PPEIII cell to a FOXN1+, PSMB11+, EPCAM+ TEPC, the method comprising culturing the ventral PPEIII cell in a medium comprising at least:

an IFN type I or II signaling pathway activator;
a FGF signaling pathway activator; and
an IGF signaling pathway activator.

15. The method of claim 14, wherein the method further comprises introducing the TEPC into a human.

16. The method of claim 12, wherein the WNT signaling pathway activator is a noncanonical WNT signaling pathway activator.

17. The method of claim 16, wherein the noncanonical WNT signaling pathway activator is CHIR99021.

18. The method of claim 16, wherein the medium further comprises a canonical WNT signaling pathway activator.

* * * * *